US005702462A

United States Patent [19]
Oberlander

[11] Patent Number: 5,702,462
[45] Date of Patent: Dec. 30, 1997

[54] METHOD OF MENISCAL REPAIR

[76] Inventor: Michael Oberlander, 2485 High School Ave., Ste. 208, Concord, Calif. 94520

[21] Appl. No.: 590,667

[22] Filed: Jan. 24, 1996

[51] Int. Cl.$^6$ .................................................. A61F 2/38
[52] U.S. Cl. ...................... 623/20; 128/898; 606/232; 606/224; 606/213; 606/220
[58] Field of Search .................... 623/13, 20; 606/1, 606/60, 62–67, 72–75, 77, 79, 87–88, 95, 101, 104, 139, 142–144, 146–148, 151, 167, 184–185, 187, 205–207, 210–211, 213, 219–220, 222–227, 232; 128/898

[56] References Cited

U.S. PATENT DOCUMENTS

| | | |
|---|---|---|
| 3,570,497 | 3/1971 | Lemole . |
| 4,635,637 | 1/1987 | Schreiber . |
| 4,738,255 | 4/1988 | Goble et al. . |
| 4,741,330 | 5/1988 | Hayhurst . |
| 4,781,190 | 11/1988 | Lee . |
| 4,873,976 | 10/1989 | Schreiber . |
| 4,895,148 | 1/1990 | Bays et al. . |
| 4,924,865 | 5/1990 | Bays et al. . |
| 4,926,860 | 5/1990 | Stice et al. . |
| 4,950,285 | 8/1990 | Wilk . |
| 4,976,715 | 12/1990 | Bays et al. . |
| 4,997,436 | 3/1991 | Oberlander . |
| 5,002,562 | 3/1991 | Oberlander . |
| 5,053,047 | 10/1991 | Yoon . |
| 5,059,206 | 10/1991 | Winters . |
| 5,102,421 | 4/1992 | Anspach, Jr. . |
| 5,154,189 | 10/1992 | Oberlander . |
| 5,254,129 | 10/1993 | Alexander . |
| 5,269,783 | 12/1993 | Sander . |
| 5,318,579 | 6/1994 | Chow . |
| 5,320,624 | 6/1994 | Kaplan et al. . |
| 5,320,633 | 6/1994 | Allen et al. . |
| 5,374,268 | 12/1994 | Sander . |
| 5,382,258 | 1/1995 | Chow . |
| 5,389,104 | 2/1995 | Hahnen et al. . |
| 5,395,375 | 3/1995 | Turkel et al. . |
| 5,500,000 | 3/1996 | Feagin et al. . |

OTHER PUBLICATIONS

*The Meniscal Anchor*, a brochure from GMI, Inc.
Justin, Daniel F., *A Needle Guided Resorbable Staple For Arthroscopic Meniscal Repair*.
DiStefano et al., *A Technique of Arthroscopic Meniscoplasty*, Orthopedics, vol. 6, No. 9, pp. 1135–1140 (1983).
Clancy et al., *Arthroscopic Meniscal Repair*, Orthopedics, vol. 6, No. 9, pp. 1125–1129 (1983).
Henning, Charles E., *Arthroscopic Repair of Meniscus Tears*, Orthopedics, vol. 6, No. 9, pp. 1130–1132 (1983).

*Primary Examiner*—John G. Weiss
*Assistant Examiner*—Francis K. Cuddihy

[57] ABSTRACT

A method for repairing a torn meniscus includes inserting at least two anchoring members into the meniscus. Each anchoring member includes a dart and at least one suture. The darts are embedded in the meniscal tissue distal to the plane of the meniscal tear, the anchoring member being inserted transversely through and across the plane of the tear. The sutures of the two anchoring members extend from the anchoring members through and across the plane of the tear and out of the meniscus. The sutures are tied together and the knot formed is drawn into contact with the surface of the meniscus with sufficient tension to approximate the tear.

10 Claims, 7 Drawing Sheets

METHOD OF MENISCAL REPAIR

BACKGROUND

1. Technical Field

The method described herein relates to a surgical procedure for file repair of tears in cartilaginous or soft tissue and, more particularly, to file repair of meniscal tissue.

2. Background of the Art

Menisci of file knee are flattened, crescent shaped bodies of fibrocartilage held in file knee capsule by ligaments. They absorb shock and facilitate file smooth articulation of file knee joint. Occasionally, as for example during athletics, file meniscal tissue can develop tears from sudden injury or torsional stress.

Equipment and techniques for file repair of fibrocartilage and soft tissue, such as meniscal tissue, are known. At one time meniscectomy was the standard treatment for such an injury. However, total or even partial removal of file meniscus has been found to lead to degenerative arthritis of file knee. For this reason, techniques have been developed for meniscal repair raffler than removal.

However, tears of meniscal tissue of the knee are relatively difficult to repair. Care must be taken to avoid damage to such structures as the popliteal artery, the peroneal nerve and the saphenous nerve. These repairs have been performed in both open and arthroscopic procedures. Typically, when such repairs have been performed arthroscopically, the operating instrumentation is deployed through small incisions which serve as knee portals. Fastening or anchoring devices are usually inserted through the meniscal tissue and across file plane of the tear. The plane of the tissue tear is the generally planar region defined by the opposing sides of file tissue at file tear location.

For example, U.S. Pat. No. 4,781,190 to Lee discloses a method of arthroscopic repair of the meniscus wherein a needle with an attached suture is shuttled back and forth across a tear. The needle must exit the skin of the patient on each pass to permit the suture to be grasped and pulled. When tightened, the suture draws the edges of the meniscal tissue at the tear into close approximation so as to facilitate healing.

U.S. Pat. No. 5,269,783 to Sander discloses a device for repairing torn meniscal tissue which includes two metal needles, each with a barbed bioabsorbable tissue anchoring section attached thereto and a suture connecting the ends of the barbed bioabsorbable anchor sections. The needles are inserted through the meniscus and across the plane of the tear until they exit the outer rim of the meniscus. They are pulled until the suture contacts the surface of the meniscal tissue, and sufficient tension is applied to draw the edges of the tear into contact. The barbed bioabsorbable anchor sections are disposed across the plane of the tear and keep it closed after the pulling force is no longer exerted on the needles. The bioabsorbable anchor sections are dimensioned such that a portion of each extends beyond the outer surface of the meniscus. The anchor sections are then cut at the meniscal surface, the needles and severed portions of the anchor sections being removed.

U.S. Pat. No. 5,320,633 to Allen et al. uses an instrument which traverses the plane of the meniscal tear and implants an H-shaped fastener across the tear to maintain the edges of the tissue in apposition.

All of these techniques involve the penetration of the meniscus on two sides, thereby creating an entrance puncture and an exit puncture, the exit puncture typically being located at the outer rim of the meniscus. Other methods are known which do not involve exit punctures through the knee.

For example, U.S. Pat. No. 5,059,206 to Winters discloses a method and apparatus for meniscal repair in which a barbed fastener is implanted such that it is disposed across the plane of the tissue tear and binds the tear without the fastener passing out of the opposite side of the meniscus. A flat proximal head biases the meniscus to keep the tear closed.

U.S. Pat. No. 5,154,189 to Oberlander discloses a device with barbed legs connected by a flexible suture portion. The device is applied to the surface of the meniscus across the tear.

In yet another method a suture anchor comprising a barbed dart and suture is implanted through the outer rim of the meniscus across the plane of a mar. The dart is implanted distal to the plane of the tear, the suture extending through the entrance puncture and outside the skin. A pledget can be applied to the suture and drawn down to the surface of the entrance puncture to tension the suture to close the sides of the tear. Alternatively another anchoring member can be inserted parallel to the first, and the sutures knotted to tension the sutures. In this method, however, the knots or pledget undesirably remain outside the knee capsule. Moreover, in drawing down the knot or pledger there is the possibility of causing damage to nerves and/or blood vessels beneath the surface of the skin.

While prior known techniques have been useful for repairing meniscal tears it is desirable to have an alternative technique which causes less trauma to the body tissue.

SUMMARY

A method of meniscal repair with anchoring members each comprising a dart and at least one suture is provided herein. The method avoids the need for an exit puncture and all portions of the sutures are located within the interior of the knee capsule.

More specifically, the method comprises inserting a first anchoring member across the plane of the tear such that the dart is substantially completely positioned in the meniscal tissue on the distal side of the tear, the suture extending transversely across the plane of the tear and out through the entrance puncture in the meniscus. The anchoring member is inserted from the side of the meniscus interior to the knee capsule. A second anchoring member is inserted in like manner. The suture portions extending outside the meniscus are then knotted together, the knot being brought down to the surface of the meniscus and tightened sufficiently to bias the edges of the meniscal tissue at the tear into close approximation. The excess suture material is then severed and removed.

BRIEF DESCRIPTION OF THE DRAWINGS

Various embodiments are described herein with reference to the drawings, wherein.

3

Figure 6:
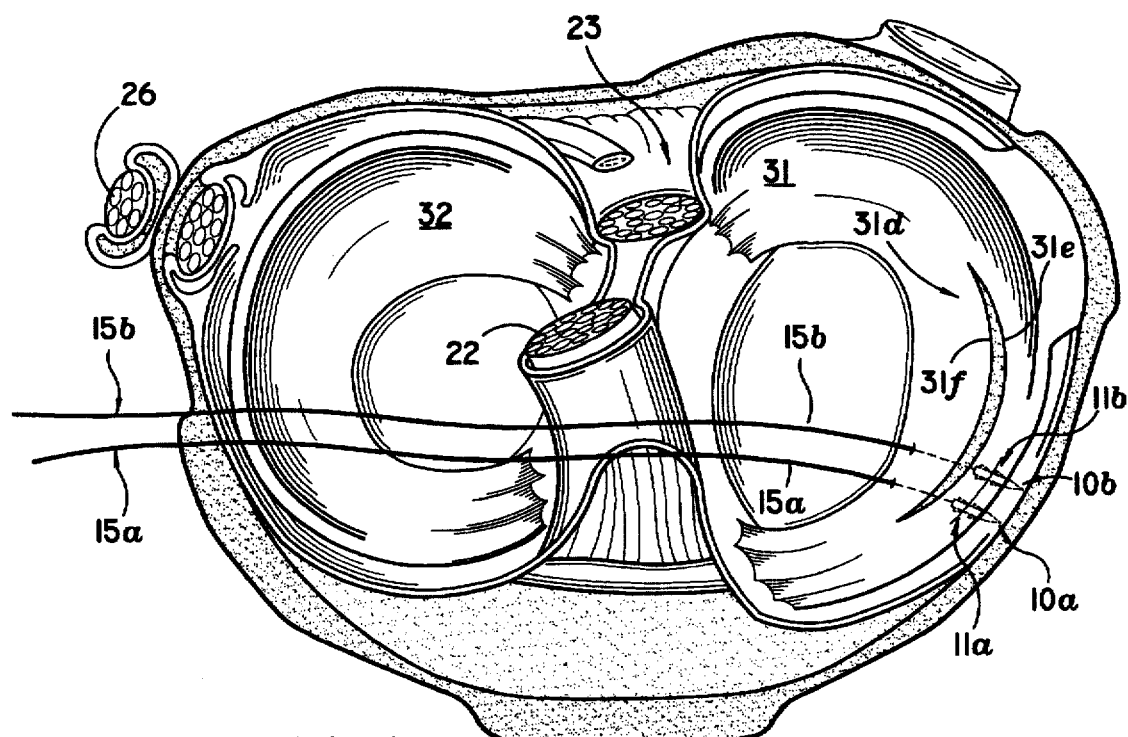
Figure 7:
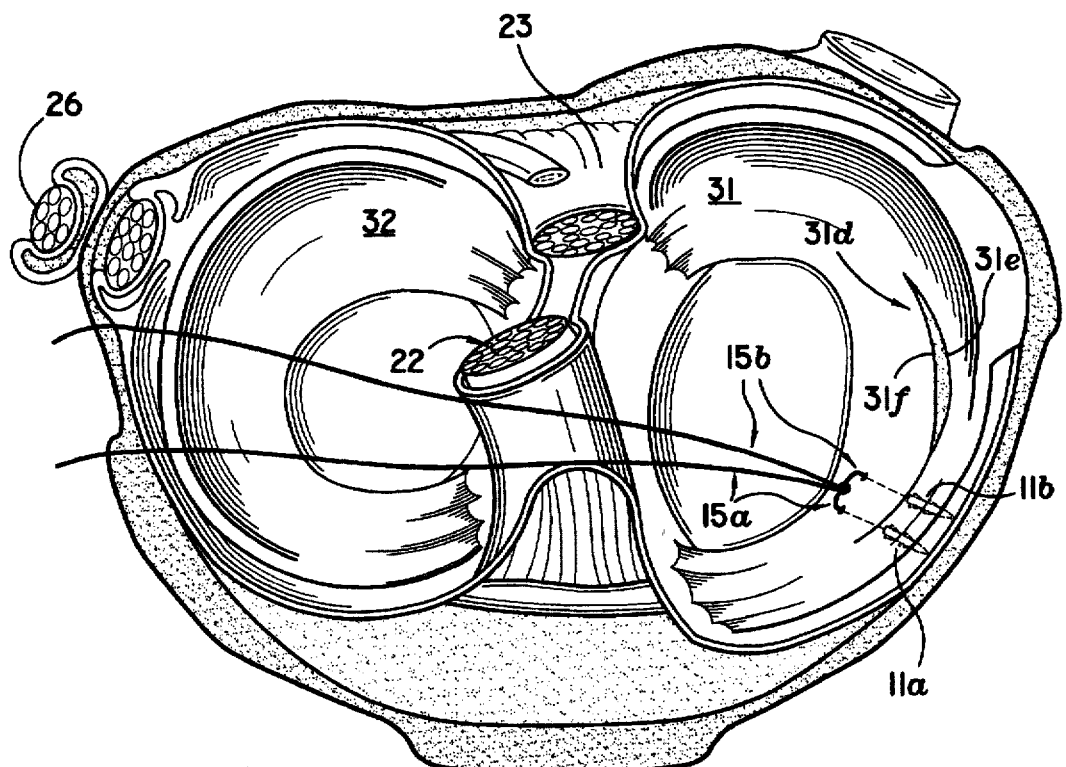
Figure 8:
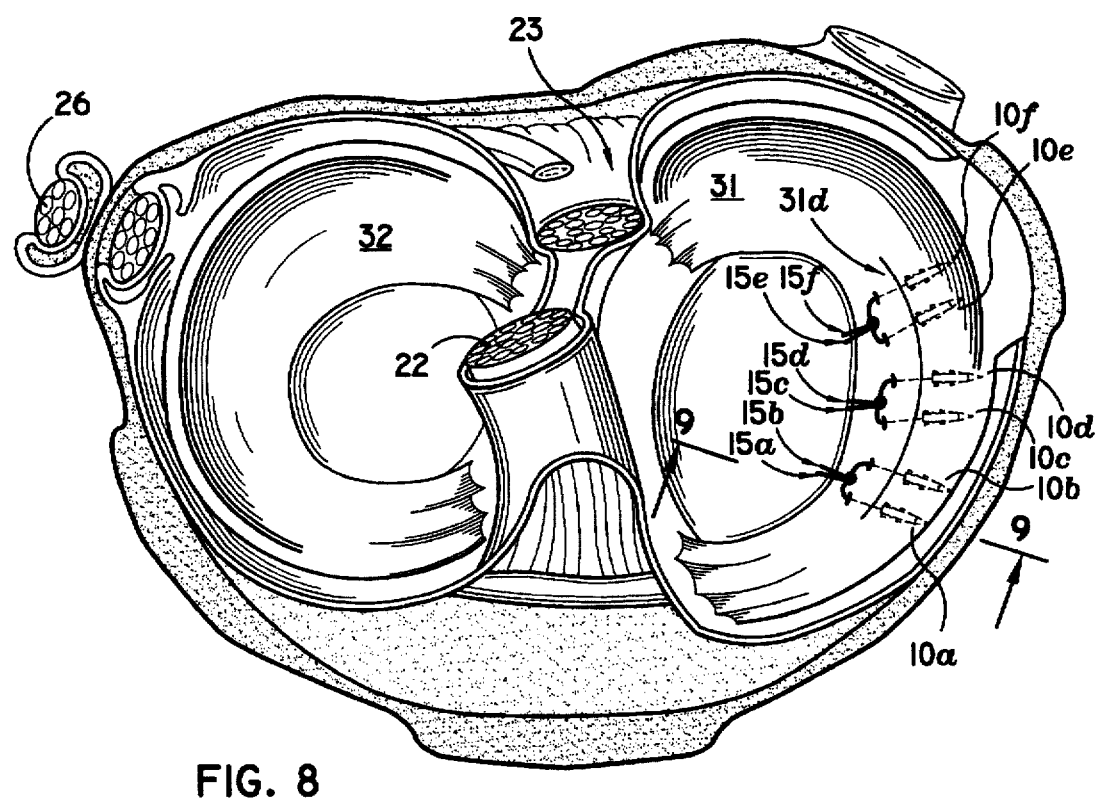
Figure 9:
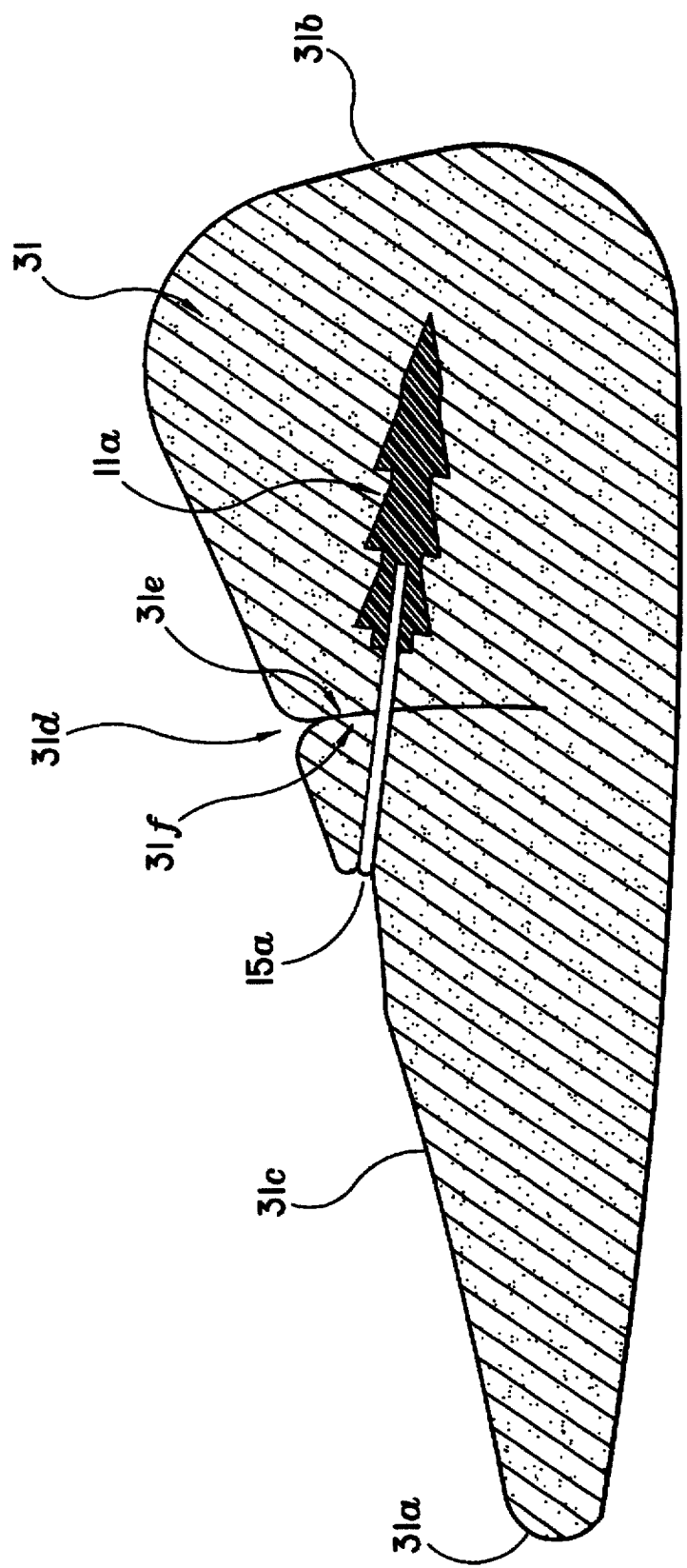
Figure 10:
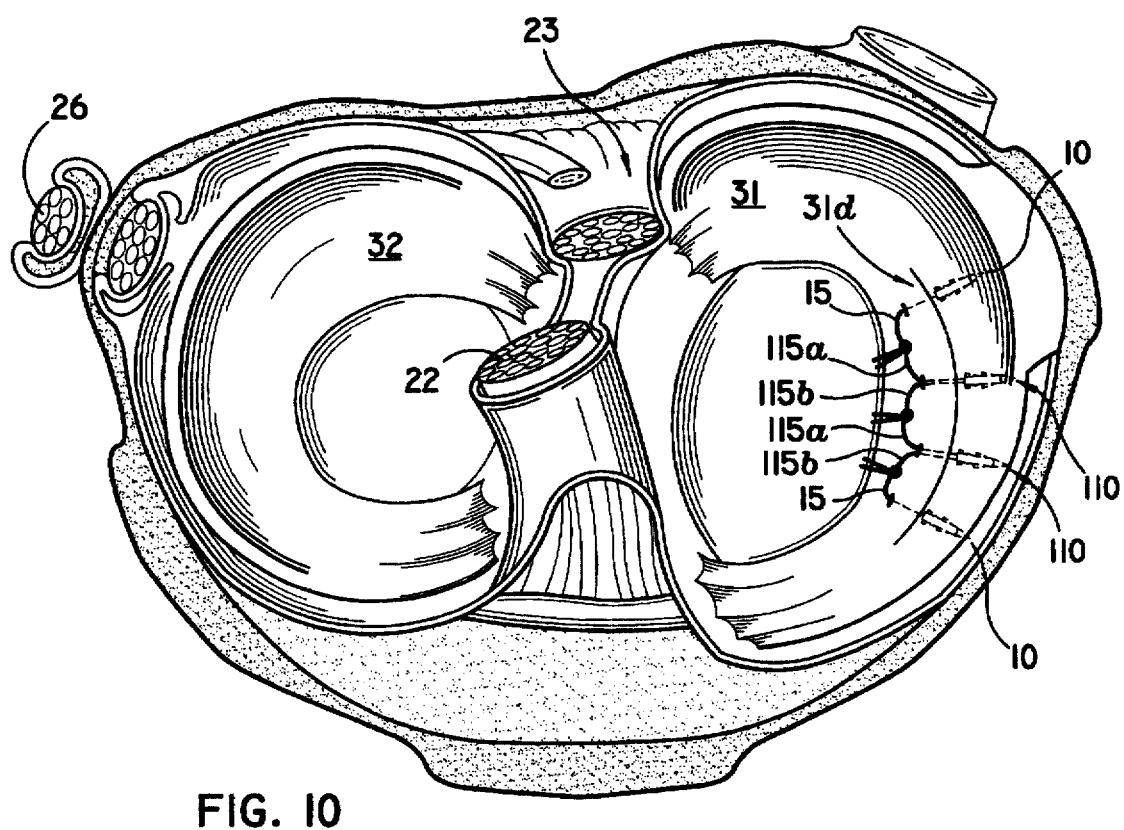

FIG. 6 is a plan view of the knee capsule showing implantation of a second anchoring member;

FIG. 7 is a plan view of the knee capsule showing the knotted sutures of the first and second anchoring members;

FIG. 8 is a plan view of the knee capsule showing the placement of three pairs of anchoring members;

FIG. 9 is a sectional view showing an anchoring member and suture implanted in the meniscus; and FIG. 10 is a plan view of the knee capsule showing the placement of the alternate embodiment of the anchoring member.

DETAILED DESCRIPTION OF A PREFERRED EMBODIMENT

As used herein the term "distal" refers to the direction in which the anchoring member is implanted. The term "proximal" is used relative to the term "distal" and refers to the direction from which the anchoring member is moved for implanting.

Figure 1:
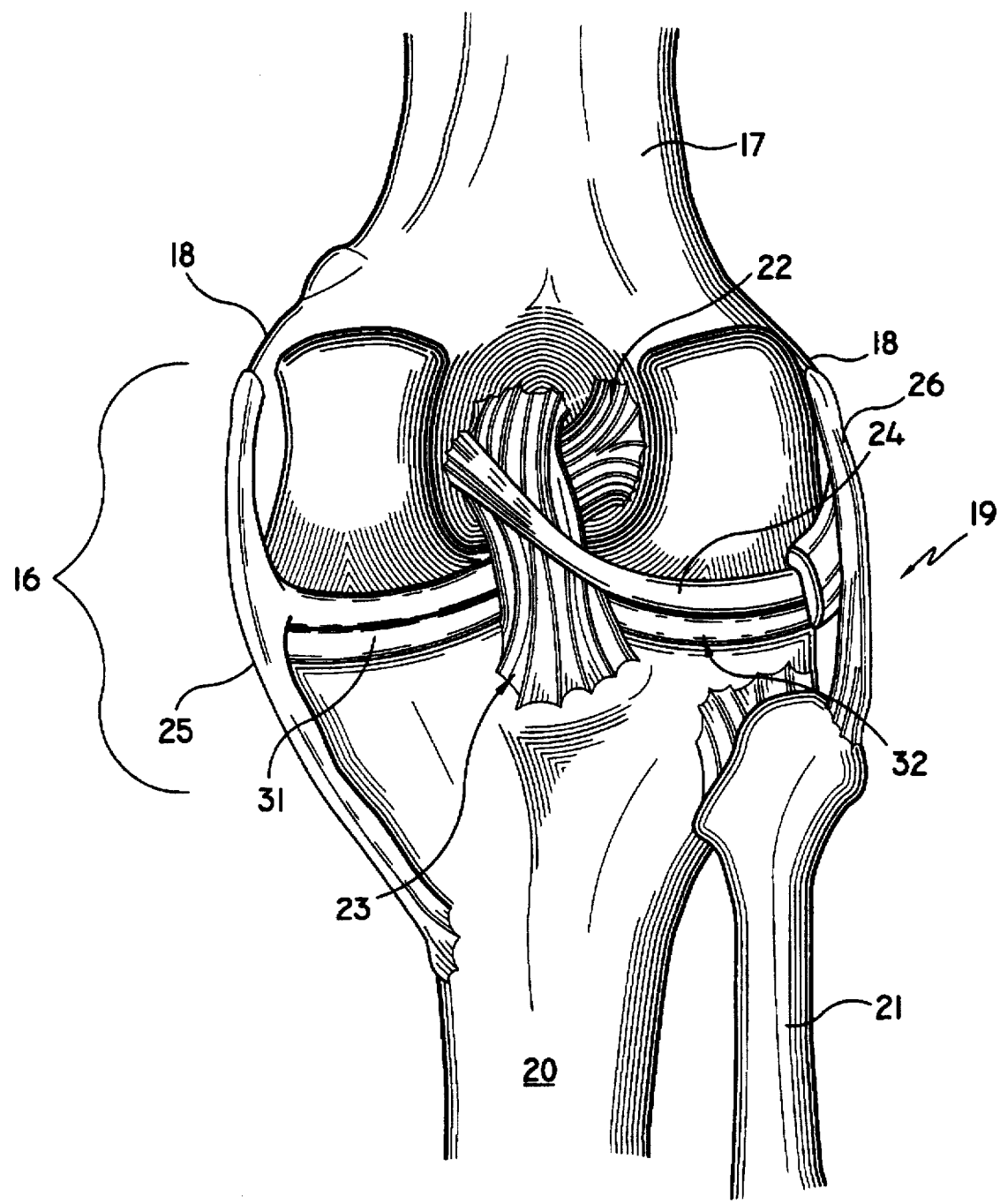
FIG. 1 is a posterior view of the knee joint of the right leg.

Referring now to FIG. 1, a posterior view of the right knee 16 shows the ligament and bone structure of the knee joint, including the pertinent components of the joint to which the repair method described herein is directed. The femur 17 includes protuberances, or condyles 18, which rest upon medial meniscus 31 and lateral meniscus 32, which are positioned in the knee capsule 19 between the femur 17 and the tibia 20. The femur 17 is joined to the tibia 20 and fibula 21 by muscles, tendons, and ligaments. The contact between these bones is cushioned by the menisci 31 and 32, which absorb shock and facilitate the movement of the joint. The bones are joined by anterior cruciate ligament 22, posterior cruciate ligament 23, ligament of Wrisberg 24, and the transverse ligament (not shown). The joint capsule 19 is further secured by tibial collateral ligament 25 and fibula collateral ligament 26.

Figure 2:
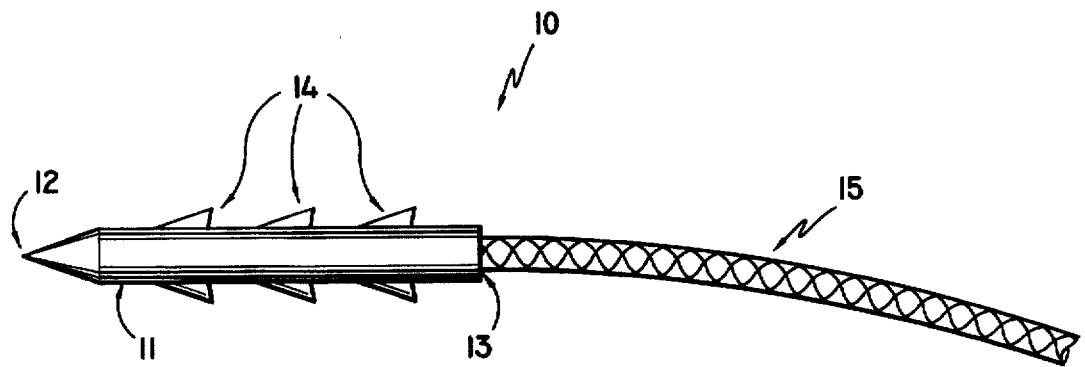
FIG. 2 illustrates the anchoring member.

FIG. 2 illustrates an anchoring member suitable for use in the method described herein. The anchoring member 10 comprises an elongated dart 11 having a distal pointed tip 12 and a bore or other means for attaching a suture at its proximal end 13. The dart preferably has barbs 14 which permit distal movement of the dart 11 through body tissue, but which resist proximal withdrawal of the dart after it has been implanted. Suture 15 is attached to the proximal end 13 of the dart and is of sufficient length for the purposes described herein. Both the dart 11 and suture 15 can be fabricated from bioabsorbable materials such as those well known in the art. Various types of darts and anchoring devices are disclosed, for example, in U.S. Pat. Nos. 5,269,783, 5,102,421, 4,895,148, and 4,873,976. Bioabsorbable compositions are disclosed, for example, in U.S. Pat. No. 5,320,624, herein incorporated by reference.

Figure 2A:
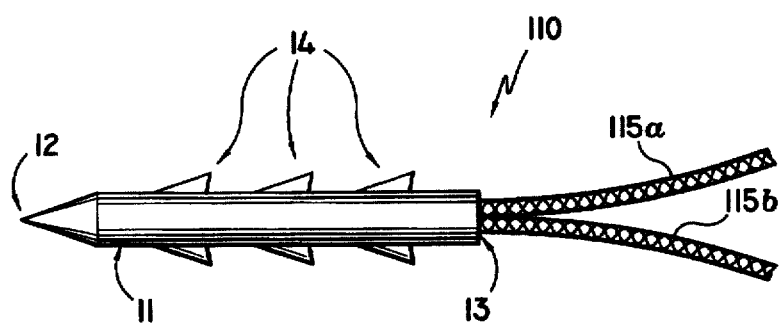
FIG. 2A illustrates an alternative embodiment of the anchoring member.

FIG. 2A illustrates an alternative embodiment 110 of the anchoring member wherein two sutures 115a and 115b are attached to the proximal end 13 of the dart 11. Anchoring member 110 allows the placement of anchoring members in odd numbers or pairs with a continuous connection of sutures, as explained below with reference to FIG. 10.

Figure 3:
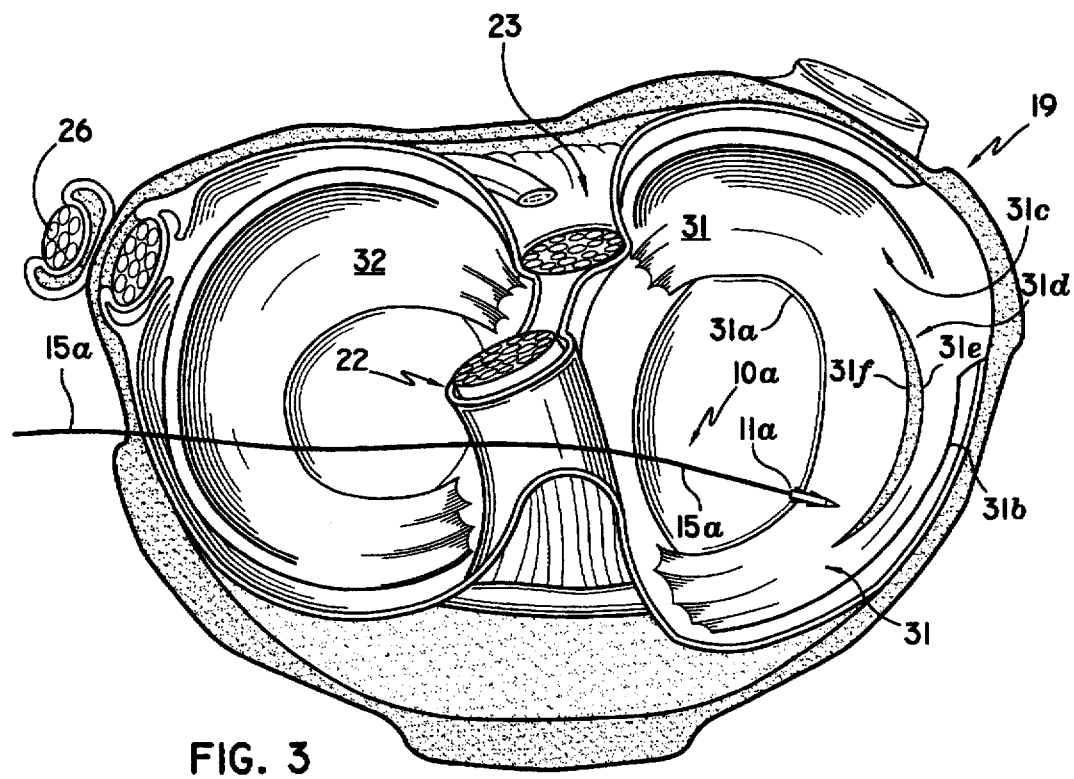
FIGS. 3 and 4 are plan views of the knee capsule respectively showing introduction of the anchoring member and insertion of the anchoring member into the torn meniscus.
Figure 4:
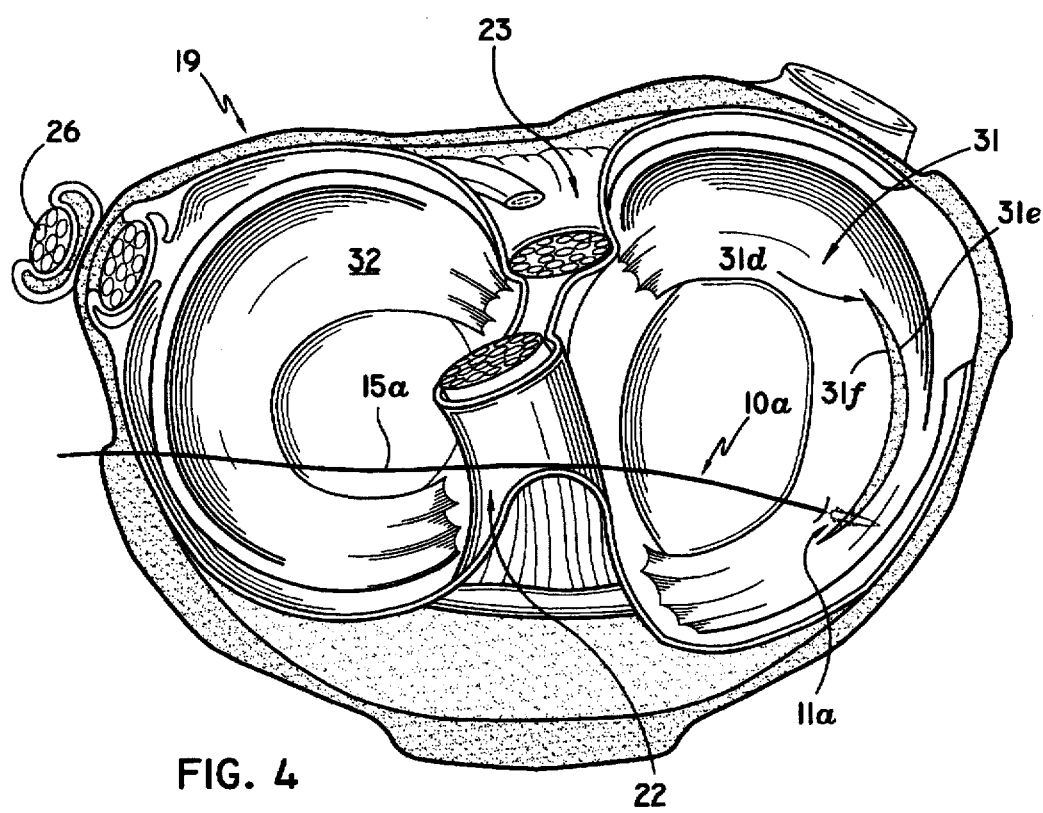
Figure 5:
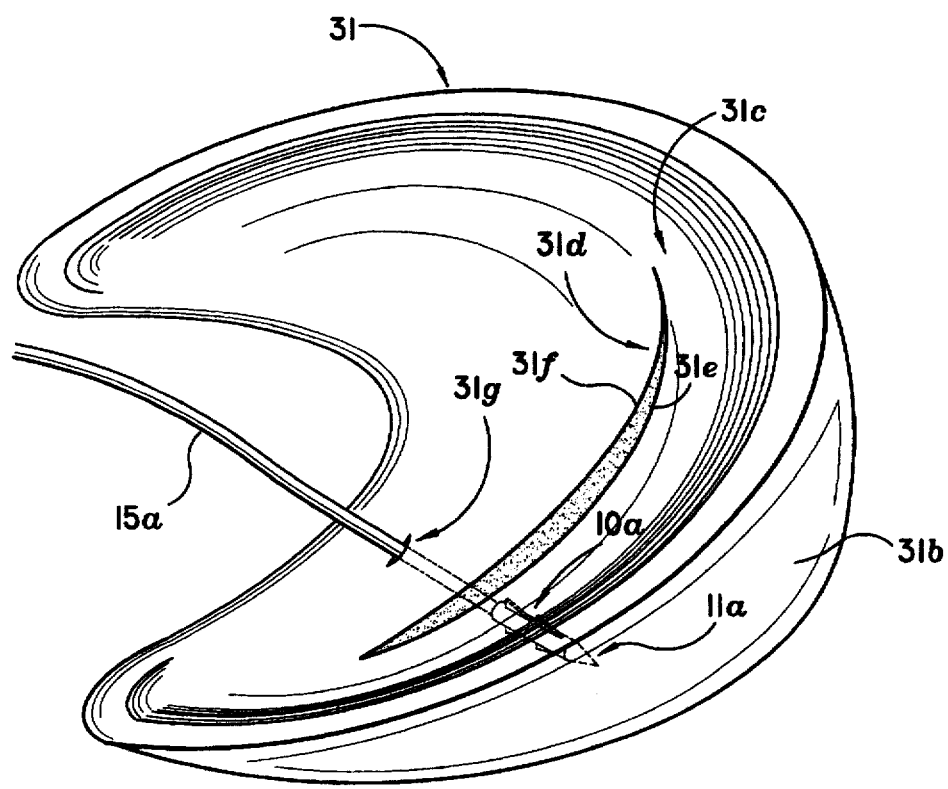
FIG. 5 is a perspective view of the torn meniscus showing placement of the implanted anchoring member.

Referring now to FIGS. 3 to 5, the interior of the knee capsule 19 is shown along with medial meniscus 31 and lateral meniscus 32. The medial meniscus 31 has an arcuate inner edge 31a, an arcuate outer rim 31b, and is thicker at the outer rim 31b than it is at the inner edge 31a. The upper side 31c of the meniscus is shown as having a tear 31d to be repaired according to the method described herein. While the medial meniscus 31 is shown as being operated upon, it will be appreciated that the method described herein is equally appropriate for the lateral meniscus 32.

An anchoring member 10a such as described above is introduced into the knee capsule by means of any applicator capable of implanting the anchoring member 10a into meniscal tissue. An applicator such as that described in U.S. Pat. No. 5,102,421 is suitable for use in the present method. The torn meniscus is preferably approached from the opposite side of the knee. Thus, for example the middle one third of the medial meniscus 31 is approached by traversing the knee capsule 19 from the lateral side and vice versa. Posterior tears would be approached from the ipsilateral portal. The anchoring member dart 11a is inserted through the upper surface 31c of the meniscus and transversely across the plane of tear 31d until dart 11a is lodged at least partially and preferably completely in the meniscal tissue distal to the distal surface 31e of the tear 31d. (FIGS. 4 and 5) That is, the proximal end 13 of the dart 11 is preferably distal to distal surface 31e of the tear. This approach enhances the effectiveness of the repair by ensuring that the anchoring member is implanted in the thicker portion of the meniscus. The suture 15 extends transversely across the plane of tear 31d and exits the meniscus 31 at the entrance puncture 31g on the upper surface 31c. A length of suture 15a extends through the knee capsule 19 and outside the surface of the skin where it can be grasped and later tied by a surgeon. As is apparent from the drawings and description herein, a proximal force applied to the suture will tension the suture 15a because the dart 11a resists proximal movement relative to the surrounding meniscal tissue. Accordingly, the tension of the suture biases the distal meniscal tissue surface 31e towards the proximal meniscal tissue surface 31f, which is the opposite side of tear 31d.

Next, as shown in FIG. 6, another anchoring member 10b having dart 11b and suture 15b is applied in a manner similar to that of anchoring member 10a. The second anchoring member 10b is of similar size and construction to anchoring member 10a and is lodged in the meniscal tissue distal to the distal surface 31e of tear 31d in a position generally parallel to (i.e., in juxtaposed alignment with) and spaced apart from anchoring member 10a relative to tear 31d. Preferably, the darts 11a and 11b are spaced apart at a distance of from about 4 mm to about 6 mm.

Next, the suture lengths exterior to the knee capsule are tied by the surgeon and an arthroscopic knot tying device is used to draw the knot tightly down upon the meniscal tissue. Arthroscopic knot tying instruments suitable for use in the present method are known and described, for example, in U.S. Pat. Nos. 5,318,579, and 5,382,258.

Referring now to FIG. 7, drawing the knot tightly down upon the meniscal tissue applies tension to the suture and thereby draws the opposing surfaces 31e and 31f of the tear 31d into contact to promote healing of the tear. A bioabsorbable anchoring member will gradually dissolve over a period of a few months, thereby providing closure of the meniscal tear for sufficient time to promote healing while obviating the need for another operation to remove the anchoring member.

Next, an arthroscopic scissor or other cutting instrument is introduced and the excess length of sutures 15a and 15b proximal to the knot are severed and removed from the knee capsule. Cutting instruments suitable for use in the present method are known and described, for example, in U.S. Pat. Nos. 5,395,375, 5,389,104 and 5,254,129.

Depending upon the length of the tear one or more pairs of anchoring members can be applied in this manner to effect substantially complete closure of the meniscal tear. For example, as shown in FIG. 8, anchoring members 10c and 10d are applied to the meniscus 31, sutures 15c and 15d being tied together to further bias the tear 31d into closure. Another pair of anchoring members 10e and 10f are also applied in a similar manner with respective sutures 15e and 15f being tied together.

FIGS. 8 and 9 illustrate that the suture extending outside the meniscus 31 is nevertheless entirely within the knee capsule 19. The outer rim 31b of the meniscus is not punctured.

Referring to FIG. 10, the placement of anchoring members 110 is illustrated. The sutures of two anchoring members 110 are connected together and to the sutures of anchoring members 10 using the insertion and tying method described above. As can readily be appreciated, anchoring members 110 allow the placement of odd numbers of anchoring members as well as even numbers. Also, the sutures can be connected in a line, as shown in FIG. 10, rather than having to be paired off. Anchoring members 110 can be employed by themselves, or preferably in combination with anchoring members 10.

As will be appreciated, the present method provides an effective arthroscopic method of repairing a tear in the meniscus of a joint. The method advantageously reduces the possibility of collateral damage to other parts of the joint anatomy.

While the above specification describes many particulars, these particulars are merely exemplifications of the preferred embodiment and should not be construed as limiting. Those with skill in the art will envision other embodiments within the scope and spirit of the disclosure as defined by the claims appended hereto.

What is claimed is:

1. A method of repairing a tear of a meniscus in a joint between bones of a human body comprising:
   (a) providing at least tint and second anchoring members, each said anchoring member comprising a dart having a distal point and a proximal end and at least one suture attached to the dart;
   (b) inserting the first anchoring member dart within and across the interior of the joint into an interior surface of the meniscus inside the joint by traversing the inside of the joint and advancing the tint anchoring member dart at least partially across a plane of the meniscal tear and lodging the first anchoring member dart in meniscal tissue distal to the plane of the meniscal tear;
   (c) inserting the second anchoring member dart within the joint into an interior surface of the meniscus inside the joint by traversing the inside of the joint, and advancing the second anchoring member dart at least partially across the plane of the tear and lodging the second anchoring member dart in meniscal tissue distal to the plane of the meniscal tear; and
   (d) tying the at least one suture of the first anchoring member to the at least one suture of the second anchoring member to form a knot, and drawing the knot into contact with the surface of meniscal tissue inside the joint with sufficient tension to approximate the tear.

2. The method of claim 1 wherein each said dart includes at least one barb, wherein said barb resists proximal movement of the dart after implantation.

3. The method of claim 1 wherein each said dart and suture are fabricated from bioabsorbable material, said bioabsorbable material being absorbed into the human body after a predetermined period of time.

4. The method of claim 1 wherein the fast anchoring member dart and the second anchoring member dart are implanted completely distal to the plane of the meniscal tear such that the proximal end of the dart is distal to the plane of the tear.

5. The method of claim 1 wherein the first anchoring member dart and the second anchoring member dart are lodged in substantially perpendicular alignment relative to the tear.

6. The method of claim 1 wherein the first anchoring member dart and the second anchoring member dart are lodged in meniscal tissue distal to the meniscal tear such that they are spaced apart from each other a distance of from about 4 mm to about 6 mm.

7. The method of claim 1 further comprising inserting third and fourth anchoring members in the same manner as the first and second anchoring members and tying the at least one suture of the third and fourth anchoring members together in a knot and drawing the knot into contact with the meniscal tissue with sufficient tension to approximate the tear.

8. The method of claim 7 further comprising inserting fifth and sixth anchoring members in the same manner as the first and second anchoring members and tying the at least one suture of the fifth and sixth anchoring members together in a knot and drawing the knot into contact with meniscal tissue with sufficient tension to approximate the tear.

9. The method of claim 1 wherein the meniscus is located in a knee capsule of a human body.

10. The method of claim 1 wherein the step of providing at least first and second anchoring members comprises providing at least fast, second and third anchoring members, the third anchoring member having two sutures attached to the dart, wherein the tying step comprises tying one of said two sutures of the third anchoring member with the at least one suture of the first anchoring member and the other of the two sutures of the third anchoring member with the at least one suture of the second anchoring member.

* * * * *